(12) United States Patent
Schoenfuss et al.

(10) Patent No.: US 9,599,596 B2
(45) Date of Patent: Mar. 21, 2017

(54) OPTICAL SENSOR ELEMENT

(71) Applicant: HAMILTON Bonaduz AG, Bonaduz (CH)

(72) Inventors: Dirk Schoenfuss, Tamins (CH); Claudius-Michael Ortega Schulte, Domat/Ems (CH)

(73) Assignee: Hamilton Bonaduz AG, Bonaduz (CH)

( * ) Notice: Subject to any disclaimer, the term of this patent is extended or adjusted under 35 U.S.C. 154(b) by 0 days.

(21) Appl. No.: 14/403,881

(22) PCT Filed: May 29, 2013

(86) PCT No.: PCT/EP2013/061139
§ 371 (c)(1),
(2) Date: Nov. 25, 2014

(87) PCT Pub. No.: WO2013/178723
PCT Pub. Date: Dec. 5, 2013

(65) Prior Publication Data
US 2015/0110687 A1 Apr. 23, 2015

(30) Foreign Application Priority Data

May 30, 2012 (DE) .................. 10 2012 104 688

(51) Int. Cl.
*G01N 31/22* (2006.01)
*G01N 21/64* (2006.01)
*G01N 21/77* (2006.01)

(52) U.S. Cl.
CPC ....... *G01N 31/225* (2013.01); *G01N 21/6428* (2013.01); *G01N 21/77* (2013.01);
(Continued)

(58) Field of Classification Search
CPC ..... G01N 1/225; G01N 21/77; G01N 21/6428
(Continued)

(56) References Cited

U.S. PATENT DOCUMENTS 3,612,866 A 10/1971 Stevens
4,919,891 A * 4/1990 Yafuso et al. ............... 422/401
(Continued)

FOREIGN PATENT DOCUMENTS

DE 3900191 A1 7/1990
DE 10101576 A1 9/2002
(Continued)

OTHER PUBLICATIONS

German Search report for corresponding priority application DE 10 2012 104 688.3 dated Jun. 12, 2012.

*Primary Examiner* — Jill Warden
*Assistant Examiner* — Jacqueline Brazin
(74) *Attorney, Agent, or Firm* — Paulding & Huber LLP

(57) ABSTRACT

The invention relates to an optical sensor element, comprising indicators (2), selected from luminescence-active means that are of the same type or different, and indicator protectors (1), and to a sensor, comprising at least one such sensor element, an energy source that excites the luminescence emission of the indicators, and a detector unit, wherein the sensor element or sensor is suitable for detecting molecular oxygen in a gaseous or liquid medium and/or for determining the molecular oxygen content of a gaseous or liquid medium and at least one layer of the sensor element bearing the indicator protectors is designed in such a way that the diffusion rate of the molecular oxygen formed on the indicator protectors by means of the reduction of strong oxidants back into the medium is greater than the diffusion rate of molecular oxygen from the medium in the direction of the at-least-one layer bearing the indicator molecules.

3 Claims, 4 Drawing Sheets

(52) U.S. Cl.
CPC . *G01N 21/6408* (2013.01); *G01N 2021/6432* (2013.01); *G01N 2021/6439* (2013.01); *G01N 2021/773* (2013.01); *G01N 2021/7786* (2013.01); *G01N 2021/7796* (2013.01); *G01N 2201/062* (2013.01)

(58) Field of Classification Search
USPC .......................................................... 422/427
See application file for complete search history.

(56) References Cited

U.S. PATENT DOCUMENTS

| | | | |
|---|---|---|---|
| 5,128,102 | A | 7/1992 | Kaneko et al. |
| 5,173,432 | A | 12/1992 | Lefkowitz et al. |
| 2001/0048072 | A1* | 12/2001 | Painchaud et al. ...... 250/227.14 |
| 2011/0236989 | A1* | 9/2011 | Suri et al. .................... 436/172 |
| 2011/0266449 | A1 | 11/2011 | Wuenn et al. |

FOREIGN PATENT DOCUMENTS

| | | | |
|---|---|---|---|
| DE | 69911062 T2 | | 7/2004 |
| DE | 69830418 T2 | | 1/2005 |
| DE | 102004033303 A1 | | 11/2005 |
| DE | 69921199 T2 | | 2/2006 |
| DE | 102012105253 | * | 12/2013 |
| EP | 1757924 | * | 2/2007 |
| EP | 1757924 A2 | | 2/2007 |
| GB | 1190583 | | 5/1970 |
| GB | 2132348 A | | 7/1984 |
| WO | 96/17012 | | 6/1996 |

* cited by examiner

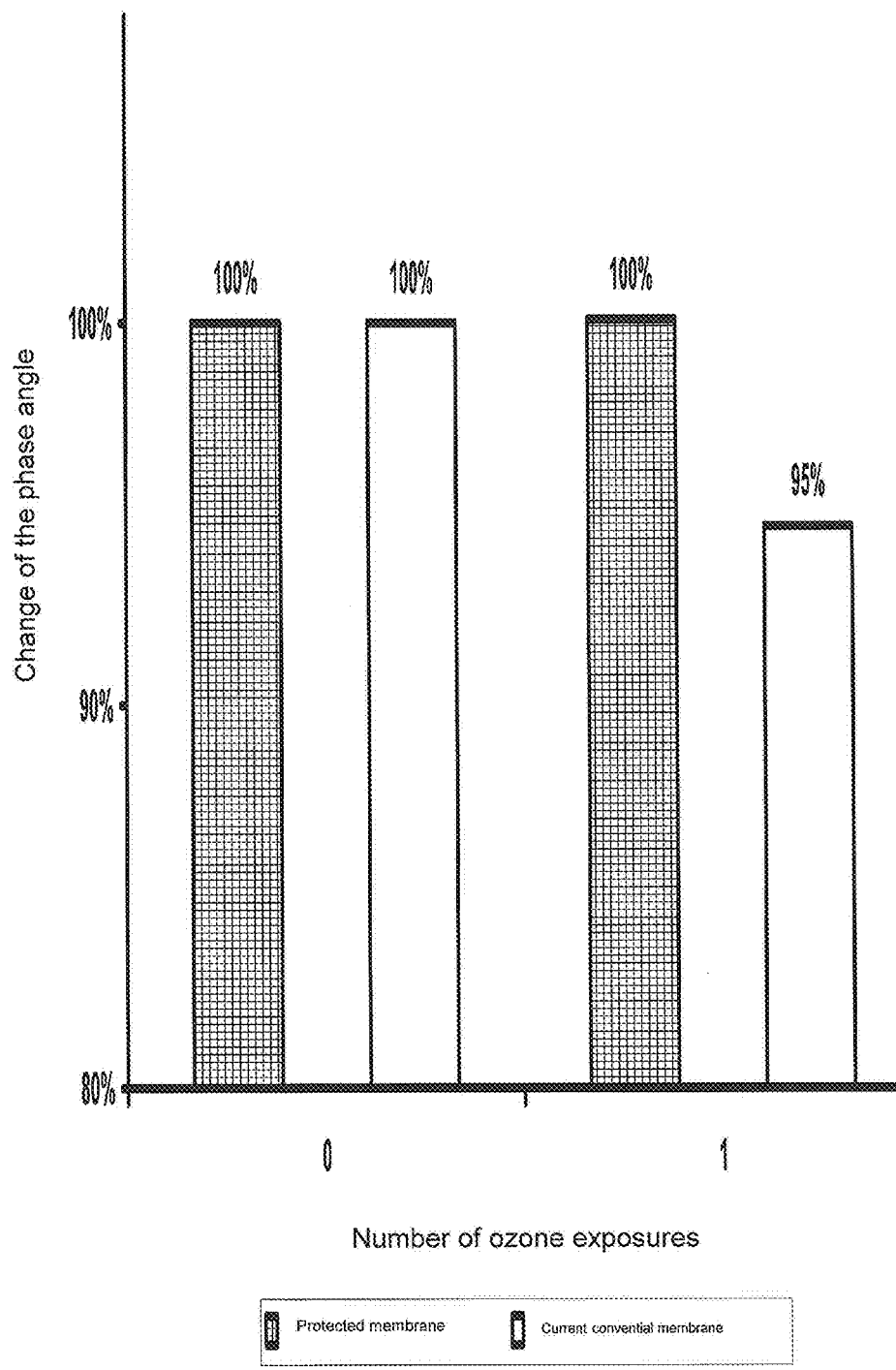

OPTICAL SENSOR ELEMENT

BACKGROUND

Technical Field

This invention relates to a sensor element and a sensor comprising this type of sensor element, where the sensor compounds (indicators) contained in the sensor element are protected against damaging or inactivating influences, such as highly reactive compounds. The invention further relates to the use of the sensor element and the sensor for determining an analyte in an environment which is aggressive for the indicator.

Discussion of Related Art

Sensor structures containing excitable sensor compounds (indicators) are generally known. The sensor principle is based on the fact that the indicators are first converted to an excited energy state by the supply of excitation energy. As the energy is released, e.g. in the form of light of a certain wavelength, the indicators switch to a lower energy level. The determination of an analyte in a sample is usually carried out by measuring the energy emitted by the indicators, which is sufficiently changed upon contact with an analyte to permit detection.

Different sensor types can be distinguished based on the form of their excitation and emission energy. The indicators of optical sensors can be excited, for example, by a supply of light, or chemical or electrical energy, although the emission always takes place in the form of light of a definite wavelength. In the case of purely optical sensors, the excitation and emission of the indicators takes place in the form of light of a specific excitation wavelength ($v_1$) and emission ($v_2$) wavelength. Optical sensors are used for example for the determination of oxygen, halide, and heavy metal ions, carbon dioxide ($CO_2$) and of the pH value. The sensor principle may in this case be based on the measurement of luminescence quenching, the change in luminescence decay time, and/or the absorption of light waves.

At present, for the optical measurement of dissolved oxygen, sensors are used which are based on the property of certain luminescence indicators, whose luminescence of wavelength $v_2$ is excited by light irradiation of a certain wavelength $v_1$, and is dynamically quenched in the presence of oxygen, such that oxygen causes the radiationless deactivation of the excited state of the luminescence indicator.

Optical sensors are widely used for the reliable determination of an analyte in complex media, because the measurement methods used here are comparatively simple and require little equipment expense. However, conventional optical sensors have the disadvantage that the sensor elements do not provide adequate protection of the indicators they contain from destructive influences, and in particular from reactive compounds in the environment being analyzed. As a result, the service life of established sensor elements is especially limited when the indicators are exposed to conditions under which they are permanently or irreversibly inactivated.

In various applications, the medium to be analyzed contains, for example, compounds which destroy the indicators due to a chemical reaction. Thus, the problem with the current state of the technology is that the optical sensor elements currently available for determining molecular oxygen either cannot be used or only with a very limited service life if the medium to be analyzed, such as waste water or water from swimming pools, contains strong oxidants such as ozone, superoxide or hydroxyl radicals or chlorine or peroxide compounds used for disinfection, the diffusion of which to the indicators in the sensor element cannot be prevented, and contact leads to the oxidative inactivation of the indicators. Due to the lack of protection for the indicators, conventional sensor elements are either not suitable or only to a very limited degree under these conditions.

There is therefore a need for optical sensors for the luminescence detection of analytes in complex media, in which the luminescence indicators of the sensor elements are effectively protected against destructive or inactivating influences from the environment being analyzed.

The sensors referred to in CN 102109488 A are only multilayered electrochemical oxygen sensors, the indicators of which are protected by a noble metal-doped layer with a catalytic function, which is arranged between the medium and the indicator-bearing layer.

Optical sensors, the sensor elements of which are effectively protected by the indicator-bearing layer or layers against attack by reactive compounds, thus enabling the long-lasting determination of an analyte by means of luminescence measurement in a (chemical) environment that is aggressive for the indicators, are not known from the prior art, nor can they be derived from it.

SUMMARY OF THE INVENTION

The present invention provides an optical sensor element, comprising
a) indicators that are selected from luminescence-active agents which are of the same type or different, depending on the intended use, and
b) indicator protectors.

The indicator protectors of the sensor element according to the invention are selected such that they protect the indicators from destructive or inactivating influences and particularly those destructive or inactivating influences to which the sensor element is exposed during its intended use.

The term "optical sensing element" in the context of the present invention includes the elements of a sensor which contain luminescent indicators. The term "luminescent indicators" refers to molecules, compounds, or substances with the property of emitting light of a definite wavelength (luminesce) following excitation by a certain amount of energy. Moreover, luminescence indicators have the property that, in the presence of a particular compound/substance or group of compounds/substances, their luminescence is characteristically altered with respect to intensity, duration, and/or wavelength. By measuring the luminescence change(s), substances that characteristically alter the luminescence of indicators which are selective for them can be determined quantitatively and/or qualitatively as an analyte, depending on the sensor construction and method of measurement. In principle, all the luminescence indicators known to specialists can be used in a sensor element constructed in accordance with the invention. Suitable luminescent indicators include, for example, chemiluminescence indicators, electro(chemi)luminescence indicators, thermoluminescence indicators, radioluminescence indicators, sonoluminescence indicators, photoluminescence indicators, and combinations of these. Fluorescent and/or phosphorescent indicators are particularly suitable for use in an element constructed according to the invention.

The sensor element according to the invention is preferably configured in such a way that it can be used in optical sensors.

The optical sensor element according to the invention may be single-layered. If the element is single-layered, the indicators and indicator protectors are contained together in one layer. In a preferred embodiment, the optical sensor element according to the invention has a multi-layered structure, with at least two layers, and preferably two, three, four, five, or six layers, where the indicators and indicator protectors are arranged in at least one of the layers of the element. The layers may be constructed and arranged so as to perform various functions within the element. The layers within the multi-layered element may differ in terms of layer thickness, composition, and/or concentration of matrix components and/or the components incorporated in it. The segmented, layered structure thus offers the advantage that the element can be specifically designed for the relevant intended use and adapted to this.

The indicator-bearing and indicator protector-bearing layer or layers of the element according to the invention are preferably designed as membranes, where the thickness of the individual layers, from 0.001 to 1 mm, preferably from 0.005 to 0.5 mm, and even more preferably from 0.01 to 0.2 mm, is adapted to the element's intended use. Membranes of low thickness in the range from 10 to 200 microns have the advantage that the diffusion rate of the analyte towards the indicators is sufficiently high to permit determination of the analyte, and light emitted from the indicator can reach the sensor's optical detection unit without detrimental transmission losses.

The indicators and the indicator protectors are preferably arranged in different layers of the multi-layered, at least two-layered, element, i.e. the element comprises at least one indicator-bearing layer, which (primarily) contains the indicators, and at least one indicator protector-bearing layer, which (primarily) carries the indicator protectors. The indicators and indicator protectors in the respective layers are preferably immobilized, to prevent their diffusion into other layers. Immobilization can be achieved, for example, through the covalent binding of the indicators and indicator protectors to matrix components of the relevant layer. Particular preference is given to a design in which at least the indicator protector-bearing layer(s) of the sensor element are substantially free of indicators.

In one embodiment, the sensor element according to the invention comprises at least one layer comprising indicators and optional indicator protectors and at least one further layer comprising indicator protectors, where the at-least-one further indicator protector-bearing layer is substantially free of indicators.

In an alternative embodiment, the sensor element according to the invention comprises at least one layer comprising indicators and at least one further layer comprising indicator protectors, where the at-least-one indicator-bearing layer is substantially free of indicator protectors and the at-least-one indicator protector-bearing layer is substantially free of indicators.

In a preferred embodiment, the optical sensor element of the present invention is designed in such a way that the indicator protectors are arranged in a (wetted) layer (1) that contacts the medium and/or arranged in at least one layer (1a) of the element that faces toward the medium and is applied to the wetted layer (2), and the indicators are arranged in at least one layer (2) which is applied to the side of the indicator protector-bearing layer(s) (1) or (1a) facing away from the medium. Particularly preferable in this case is that the layer (1) and/or the at-least-one layer (1a) are substantially free of indicators. In addition to the indicators, the at-least-one layer (2) may also contain indicator protectors. It is preferably substantially free of indicator protectors.

An at least two-layered structure, in which there is at least one indicator-free or substantially indicator-free indicator protector-bearing layer situated upstream from the at-least-one indicator-bearing layer on the media side, offers the advantage that all of the indicators incorporated in the sensor element according to the invention receive equally effective protection from inactivating/destructive influences from the medium.

A preferred embodiment of (I) of the sensor element according to the invention comprises the following layered structure:

A layer (1) with a side (1.1) that faces the medium and contacts the medium, and a side (1.2) that faces away from the medium, situated opposite side (1.1), where this medium-contacting layer (1) comprises the indicator protectors and is preferably substantially free of indicators.

A layer (2) with a side (2.1) that contacts layer (1) and a side (2.2) situated opposite side (2.1), where layer (2) is applied to side (1.2) of layer (1) and includes the indicators and optional indicator protectors.

Optionally one or more further layers (2), which is or are applied to the already present layer (2) and optionally may include indicators and indicator protectors.

Optionally at least one further layer (1A) can be arranged between layer (1) and the at-least-one layer (2), which may comprise indicator protectors and is preferably substantially free of indicators.

A further preferred embodiment (II) of the sensor element according to the invention, in contrast to the embodiment (I) described above, is designed such that the layer (1) in contact with the media is free of indicators and also free of indicator protectors and the at-least-one further layer (1A) is mandatory.

Type, amount, and distribution of the indicator protectors in the layers (1) and, where applicable, (1A) and (2) of the sensor element may be different. There is preferably a lower proportion of indicator protectors contained in layer (2), which also contains indicators, than there is in layer (1) and/or in the at-least-one further layer (1A).

Layer (1) and in particular its side (1.1) may be designed as an opaque optical isolation layer, in particular when photoluminescence indicators are used. Furthermore, the at-least-one further layer (1A) and/or (2) can itself be light-reflecting. This has the advantage of increasing the sensitivity of the measurement when the sensor element is used.

In a particularly preferred embodiment, the element according to the invention comprises i) an optional, media-contacting opaque layer (1), which is substantially free of indicators and optionally contains indicator protectors, ii) a second layer (1A), which (iia) is applied to the side of the first layer (1) facing away from the medium, (iib) contains indicator protectors, (iic) is substantially free of indicators and (iid) is optionally light-reflective, (iii) a third layer (2) which (iiia) is applied to the side the second layer (1A) facing away from the medium, (iiib) contains the indicators, (iiic) is substantially free of indicator protectors and (iiid) is optionally light-reflective.

To further increase the sensor sensitivity of the optical sensor element described here, the indicator protector-bearing layer(s) can be separated from the indicator-bearing layer(s) by at least one light-reflecting layer, which is neither an indicator protector-bearing layer or an indicator-bearing layer.

Furthermore, a transparent substrate can be arranged on the side of the indicator-bearing layer facing away from the medium or, in the case of several indicator-bearing layers, on the outermost indicator-bearing layer opposite the medium. The transparent substrate is transparent to the light emitted by the indicator or indicators used and also transparent to the excitation light, if the excitation of the indicators is accomplished using light. The transparent substrate is preferably selected from glass, plastic, and fiber glass. It is advantageous to couple the indicator-bearing layer(s) to an optical system via the transparent substrate. The optical system may be a system known to specialists, comprising a detection/measurement unit detecting or measuring the emission, an evaluation unit, and a means of exciting the luminescence of the indicators, e.g. a light source if photoluminescence indicators are used.

The layer or layers of the element according to the invention, in particular the layers (1), (1a) and (2) and any intermediate layers are arranged in such a way that it is or they are permeable for the analyte(s). The matrix component of the layer or layers, in particular of layers (1), (1a), and (2) and any intermediate layers of the element is preferably selected from a polymer or polymer mixture. In the case of a multilayered embodiment of the element according to the invention, the matrix part may differ in the individual layers in terms of type, concentration, and/or degree of crosslinking of the polymer building blocks. Moreover, within a layer, the concentration and/or the degree of crosslinking of a matrix component or the concentration of a component incorporated in the layer can vary in a gradient manner.

It is particularly preferably that the matrix component is a polymer or polymer mixture, selected from polystyrene, polyvinyl chloride, polyalkylene methacrylate, in particular polymethyl methacrylate, polyisobutyl methacrylate and poly-2-hydroxyethyl-methacrylate, poly-a-methylstyrene, silica gels, sol-gels, hydrogels, polyurethanes, polytetrahydrofurans, polytetrafluoroethylene, polyester, polybutadiene, polyvinyl butyral, polyethyl acrylate, ethyl cellulose, cellulose triacetate, cellulose acetyl butyrate, polysulfones, polysulfides and non-, partially or fully fluorinated silicones and combinations of these, optionally in combination with plasticizers.

Layers having light-reflecting properties preferably contain pigments and in this case preferably metal oxides such as $TiO_2$ and $Al_2O_3$, semi-metal oxides such as $SiO_2$, and combinations of these.

Opaque layers preferably contain light stabilizers, for example, dark-colored and/or black pigments such as carbon black, graphite, activated carbon, or combinations of these.

As mentioned above, the sensor element according to the invention contains indicators which have the property of luminescing after excitation, and at least one of their luminescence properties changes measurably on contact with one or more analytes. Especially suitable for the present invention are indicators whose luminescent emission is selectively quenched on contact with at least one analyte.

The invention considers analytes selected from a species of oxygen, in particular molecular oxygen, carbon monoxide, carbon dioxide, halide ions, heavy metal ions, hydroxyl ions, hydronium ions, aromatic compounds, and combinations of these. However, the sensor element according to the invention is not restricted to the determination of these analytes.

In one embodiment, the sensor element according to the invention comprises luminescent indicators, in particular photoluminescent indicators the luminescence emissions of which are selectively quenched by contact with oxygen, and preferably molecular oxygen. Particularly preferred are indicators the luminescence emissions of which are dynamically quenched in the presence of oxygen, such that contact with oxygen causes the radiationless deactivation of the excited state of the luminescence indicators. Luminescent indicators that are particularly suitable for the determination of oxygen, including the complexes ruthenium, rhenium, rhodium, iridium, and lanthanide, as well as metallated porphyrins (e.g. platinum and/or palladium-porphyrins), unmetallated porphyrins, or mixtures of these, optionally in combination with fluorinated dyes and/or light stabilizers. The luminescent indicators suitable for the various applications are described in detail in the literature.

The proportion of the indicators in relation to the relevant indicator-bearing layer is up to 20 percent by weight, preferably up to 10 percent by weight, and more preferably up to 5 percent by weight. The proportion of the indicators can be adapted to the relevant application and may, if necessary, be more than 20 percent by weight.

In the context of the present invention, indicator protectors are a means to protect the luminescent indicators prior to their destruction/inactivation by external influences. The protection of the indicators is achieved by inactivation, neutralization and/or adsorptive immobilization of compounds and/or by inactivation, neutralization/insulation of energy-rich radiation, which has an inactivating and/or destructive, especially oxidizing, effect on the indicators.

Suitable indicator protector(s) include reactants of one or more compounds/substances which act on the indicators in a destructive/deactivating manner upon contact with them. The reactants react with the compounds/substances, which have a destructive/inactivating effect, e.g. in a chemical reaction, to become at least one product that is harmless for the indicators. The term "indicator protector(s)" in this context is not limited to the reactants, which upon reaction with the compound/substance that destroys/inactivates the indicator is converted into at least one new compound which is not or is less destructive or inactivating for the indicator. The term "indicator protector(s)" also refers to agents which have a catalytic effect (catalyst), and which catalyze the conversion of the indicator destroying/inactivating compound/substance to at least one new compound that is not or is less destructive or inactivating for the indicator. In this context, a "catalyst" or "agent of catalytic conversion", apart from having a purely catalytic effect, also includes compounds that, in addition to the said catalytic effect, also have a simple chemical reactivity, in the sense of a reactant which is itself converted during the reaction.

Furthermore, suitable indicator protector(s) include adsorbents of one or more compounds/substances which have a destructive/inactivating effect on the indicators upon contact. Adsorbents completely or partially inhibit the diffusion of the indicator destroying/inactivating compound/substance in the direction of the indicators.

Also particularly suitable as indicator protectors are combinations of the above reactants, catalysts and/or adsorbents. It is also possible that agents employed as indicator protectors act simultaneously as reactants, catalysts and/or adsorbents.

A sensor element according to the invention which is suitable for determining molecular oxygen and/or a sensor element according to the invention which comprises oxidation-sensitive indicators, preferably contains indicator protectors, which are selected from a) reactants, in particular reducing agents and/or catalysts, which cause a reduction of strong oxidizing agents,
b) adsorbents, which cause chemical and/or physical adsorption of strong oxidizing agents,
c) a combination of (a) and (b).

The term "strong oxidants" refers to compounds/ substances which are capable of dissociating carbon-carbon single bonds and/or carbon-hydrogen bonds, and/or in terms their electron donor and electron acceptor properties are comparable with chlorine, ozone, superoxides, hydroxyl radicals and/or peroxide radicals.

A sensor element according to the invention which is designed to determine molecular oxygen and/or a sensor element according to the invention which comprises oxidation-sensitive indicators more preferably contains indicator protectors, which are selected from a) reactants, in particular reducing agents and/or catalysts for the reduction of halogens, in particular chlorine, ozone, hydroxyl radicals, peroxy radicals and/or superoxides, b) adsorbents for chemical and/or physical adsorption of halogens, in particular chlorine, ozone, hydroxyl radical, peroxide radicals and/or superoxides
c) a combination of a) and b).

As indicator protectors suitable for the reduction of strong oxidizing agents, it is possible, in the sensor element according to the invention, to use redox-active polymers, which contain oxidizable functional groups that can react with strong oxidizing agents, but under normal conditions, for example in the air, are stable. These polymers may be incorporated as layers, as particles, or as components of copolymer in the indicator protector-bearing layer or layers. Moreover, these polymers can also act both as a matrix material and as indicator protectors. In the case of a chemical attack by strong oxidants, the functional groups of these polymers are oxidized and thus prevent or reduce the oxidative attack on the indicators, because at least part of the oxidizing agent does not reach the indicator molecules.

In a specific embodiment of the invention, the indicator protector-bearing layer or layers consist of one or more redox-active polymer(s) containing oxidizable functional groups, and optionally further containing light protection agents as defined herein.

As indicator protectors with a redox-catalytic and/or adsorptive effect, it is possible, in the sensor element according to the invention, to use agents comprising activated carbon, zeolites, metal oxide, and/or materials comprising a semiconductor oxide. These indicator protectors can be wholly or partially loaded with precious metals such as platinum and/or palladium. Such agents are familiar to specialists in the field. They are capable, if necessary with the help of water, of reducing strong oxidizing agents such as chlorine, ozone, and oxygen radicals and/or to slow their diffusion by adsorption. In this case, it is advantageous for the indicator-bearing layer(s) to be selected from polymeric matrix materials which permit the presence of water in the immediate vicinity of the catalyst as a reactant in an adequate, but a small, amount and which absorb this from the environment.

It is advantageous to select the indicator protectors such that they do not adsorb and/or do not inactivate/neutralize the analyte(s). If the sensor element according to the invention should be suitable, for example, for the determination of molecular oxygen, then the indicator protectors should be selected such that they do not adsorb and/or reduce molecular oxygen.

The indicator protectors are preferably located in the at-least-one indicator protector-bearing layer in the form of particles having a diameter of 0.1 to 200 microns, more preferably from 0.2 to 100 microns, and most preferably from 0.5 to 50 microns. Depending on the purpose, type, and quantity of the indicator protectors in the at-least-one indicator protector-bearing layer, the particle sizes may deviate from the specified values.

The particle size distribution of the indicator protector particles in the at-least-one indicator protector-bearing layer is preferably in the range 100 microns or less (100%), more preferably 50 microns or less (100%), and most preferably 30 microns or less (100%).

To effectively protect the indicators from damaging influences, the proportion of the at-least-one indicator protector-bearing layer accounted for by the indicator protectors is at least 2 percent by weight, preferably from 2 to 75 percent by weight, and more preferably 20 to 50 percent by weight. Depending on the purpose and type of the indicator protectors, the proportion of the at-least-one indicator protector-bearing layer accounted for by the indicator protectors may deviate from the specified values. If activated carbon is used as an indicator protector, the proportion of the indicator protector-bearing layer for which it accounts can be up to 80 percent by weight as appropriate, and preferably up to 50 percent by weight.

Indicator protectors comprising activated carbon are particularly suitable for protecting the photoluminescence indicators referred to herein from strong oxidizing agents. Particular preference is given to activated carbon with a BET value of at least 1000 m2/g and/or an iodine number of 1000 mg/g. Activated carbon has the advantage that, in addition to its redox-catalytic and/or adsorptive effect on the substances or compounds which destroy/inactivate the indicators, it also provides protection against the ingression of extraneous light from the media side.

In a particularly preferred embodiment, the sensor element according to the invention comprises
  indicators selected from photoluminescence indicators as defined herein, in particular from the complexes ruthenium, rhenium, rhodium, iridium, lanthanide, of from metallated porphyrins (e.g. platinum and/or palladium-porphyrins), unmetallated porphyrins, or mixtures of these, optionally in combination with fluorinated dyes/ or light stabilizers,
  indicator protectors selected from activated carbon as defined herein, optionally wholly or partially loaded with precious metals such as platinum and/or palladium.

If, in the element according to the invention, indicator protectors are used which, when the element is used to determine molecular oxygen in a gaseous or liquid medium, cause the reaction of strong oxidants, a certain amount of additional oxygen can occur as the product of this reaction. To prevent distortion of the measurement of the actual analyte, the diffusion conditions in the membrane are determined, according to the invention, by the position of the indicator protectors near the wetted surface, by their quantity, and by the type and thickness of the polymers used for the individual layers, such that the additional oxygen produced by the indicator protectors diffuses back into the solution much faster than it diffuses into the indicators, and the diffusion gradient within the layer(s) of the element hardly changes, since differences in concentration in the liquid or gaseous medium are equalized much faster there, due to the presence of convection, than in the membrane phase. The small amount of additional oxygen generated does not cause any detectable distortion of the measurement, provided the volume of medium corresponds to the surface of the sensor layer in contact with the medium.

A further object of the present invention is a sensor comprising at least one sensor element according to one of the preceding claims. This may further comprise an energy source which is familiar to specialists in the field and which excited the luminescence emission of the indicators, and may also comprise an evaluation unit.

In a preferred embodiment, the sensor element according to the invention as described above or a sensor according to the invention comprising such a sensor element for detecting molecular oxygen in a gaseous or liquid medium and/or for determining the molecular oxygen content of a gaseous or liquid medium and characterized in that at least one indicator protector-bearing layer of the sensor element is designed such that the diffusion rate of the molecular oxygen formed on the indicator protectors by the reduction of a strong oxidant back into the medium is greater than the diffusion rate of molecular oxygen from the medium in the direction of the at-least-one indicator molecule-bearing layer.

The sensor element or sensor according to the invention can be used for the quantitative and/or qualitative determination of one or more analytes, and is preferably used for the detection of molecular oxygen in a gaseous or liquid medium and/or for the determination of the molecular oxygen content of a gaseous or liquid medium. The medium, which may include complex media such as waste water or body fluids, can contain compounds which act on the indicators themselves in an inactivating and/or destructive manner. Since the indicators inside the sensor element according to the invention are effectively protected against inactivating and/or destructive compounds, their presence does not result in a greatly shortened service life of the sensor element, as is the case with the sensor elements known from the prior art.

The present invention also relates to a method of quantitatively and/or qualitatively determining one or more analytes in a medium, which involves bringing the medium into contact with a sensor as defined herein, such that this bringing-into-contact takes place on the wetted layer (1) of the sensor element.

The present invention particularly relates to a method of quantitatively and/or qualitatively detecting molecular oxygen in a medium, which may include compounds which act in an inactivating and/or destructive, in particular oxidizing, manner on the indicators themselves, such as, for example, halogens, in particular chlorine, ozone, hydroxyl radicals, peroxide radicals and/or superoxide. Such strong oxidants are used, sometimes in high concentrations, in waste water or swimming pools for disinfection purposes. The medium to be analyzed may also be a body fluid. The element according to the invention can therefore be used as part of an in vitro method for determining the oxygen content in the blood.

The method according to the invention preferably further involves the detection of the analyte(s) by measuring the intensity and/or decay time of the luminescence emission of the indicators and/or measuring the quenching of the luminescence by means of phase modulation.

The invention described above is explained in more detail below by way of the example of a sensor element designed for use in an optical oxygen sensor, without being restricted to this sensor element.

Thus, the first side (1.1) of the layer (1) of the sensor element that directly contacts the medium may be colored black to absorb light from the environment and prevent it from passing into the indicator-bearing layers. This optical insulation can be implemented by the incorporation of, for example, soot particles or activated carbon particles as described above.

There is at least one, and preferably one, two, or three indicator-bearing layers (2) applied to the side (1.2) of the layer (1) situated opposite the side (1.1) in contact with the medium. The indicators are photoluminescence indicators, which are oxygen-sensitive, i.e., their luminescence emission is selectively quenched by contact with molecular oxygen, preferably the complexes ruthenium, rhenium, rhodium, iridium, lanthanide, as well as metallated porphyrins (e.g. platinum and/or palladium-porphyrins), unmetallated porphyrins, or mixtures of these, optionally in combination with fluorinated dyes and/or light stabilizers. The at-least-one indicator-bearing layer (2) may further comprise indicator protectors.

Optionally, at least one further layer (1A) can be arranged between layer (1) and layer (2), which comprises the indicator protectors and is preferably substantially free of indicators. Furthermore, the at-least-one further layer (1A) and/or (2) can itself be light reflective, or they can be separated from each other by at least one light-reflecting layer, which is neither an indicator protector-bearing layer nor an indicator-bearing layer, so that more of the excited luminescence light is reflected onto the photodetector, which increases the luminescence output.

A transparent substrate is arranged on the side of the indicator-bearing layer facing away from the medium, or in the case of several indicator-bearing layers, on the outermost indicator-bearing layer (2) opposite the medium, which can be made from glass or plastic which is permeable to excitation light and emission light. Adjacent to this is an optical system, comprising an excitation light source such as a light-emitting diode (LED), a photodetector, usually consisting of photodiodes, corresponding optical filters, and an evaluation unit. The excitation and emission light can be transmitted, for example, through optical fibers.

Various measurement methods can be used to detect the luminescence quenching by oxygen. It can be carried out using intensity measurements, by measuring the luminescence decay time, or using the so-called phase modulation technique. The sensory principle, which is based on the phase modulation technique, consists in the excitation of the luminescence of the indicators with a specific excitation light of wavelength $v_1$, which is intensity-modulated to a frequency corresponding to its decay time. Due to the modulation of the excitation light, the resulting luminescence of the indicator with wavelength $v_2$ is also modulated. From the modulations of the excitation light and the luminescence light, a phase shift can be calculated based on the average luminescence lifetime of the excited states of the indicator molecules. The oxygen diffusing through the layer(s) from the medium being measured to the indicators affects the lifetime of their excited states in such a way that there is a radiationless transition of energy from the excited indicators to the oxygen. Corresponding to the ratio of oxygen and excited indicators in the membrane, the average lifetime is reduced and the determined phase angle becomes smaller as the amount of oxygen increases. The phase modulation technique has the advantage that the measured phase angle does not depend on the signal intensity, provided the luminescence intensity is sufficiently large to permit a correct measurement with the optical system. With appropriate calibration, it is possible to determine the partial pressure of the oxygen dissolved in the medium being investigated from the particular phase angle, using the so-called Stern-Volmer relationship. The partial pressure of oxygen can then be converted into other physical units.

Essentially responsible for the photo-induced destruction of the indicator is the reactive singlet oxygen, which is produced by the radiationless transition of energy from the indicator to the oxygen molecule, and chemically attacks the indicator. This can be counteracted by adding light stabilizers such as HALS (hindered amine light stabilizer) to the indicator-bearing layer, as disclosed, for example, in EP 1757924B1. However, the light stabilizers alone cannot provide adequate protection against e.g. chlorine. For instance, when porphyrins are used as indicators they are ultimately converted by dissolved chlorine gas to chlorins and bacteriochlorins, which results not only in the intensity of the luminescent light decreasing as the exposure increases, but also in the luminescence light being superimposed and/or absorbed by reaction products produced by the destruction of the indicator, and the relationship between the phase angle and the oxygen partial pressure as described above loses its validity. This is particularly disadvantageous, because the above-mentioned oxidants, due to their oxidation potential, are used for disinfection purposes in water treatment, which also precedes all processes in pharmaceutical biotechnology and in food production. The sensor element can be exposed to high concentrations of such oxidants, for example, in cleaning and disinfection processes, and unless the indicators are protected against these oxidants it can lose its sensitivity. Furthermore, certain reactions, e.g. in biotechnological processes, which should be monitored with the aid of an oxygen sensor, can produce strong oxidants. An example of this type of reaction is found in the metabolic process, where the reduction of molecular oxygen in the respiratory chain results in the formation of superoxide.

Thanks to the protection of the indicators in the sensor element according to the invention, it is possible to significantly extend its service life in the presence of highly oxidative chemical species in at least partially aqueous measurement media. The protection is achieved here by the protectors located in the at-least-one indicator protector-bearing layer, which cause a total or partial reduction and/or adsorptive immobilization of the oxidative chemical species, and thus prevent or diminish the attack of this chemical species on the indicators.

In the present example, catalyst particles made from activated carbon or zeolites, metal oxides, or semiconductor oxides, with or without a precious metal loading, for example, of Pt and/or Pd, or other e.g. vitreous carrier materials are used as indicator protectors. In order to achieve a stabilizing effect against oxidative attacks, the quantity of immobilized catalyst should be at least 10 percent by weight relative to the mass of the catalyst-bearing layer. The average diameter of the catalyst particles is in the sub-millimeter range, preferably in the range from 0.5-50 microns.

BRIEF DESCRIPTION OF THE DRAWINGS

FIG. 4 shows the changes in the phase angle between a sensor element according to the invention and a sensor element known from the prior art, in each case following exposure to ozone.

DETAILED DESCRIPTION OF EMBODIMENTS

Figure 1:
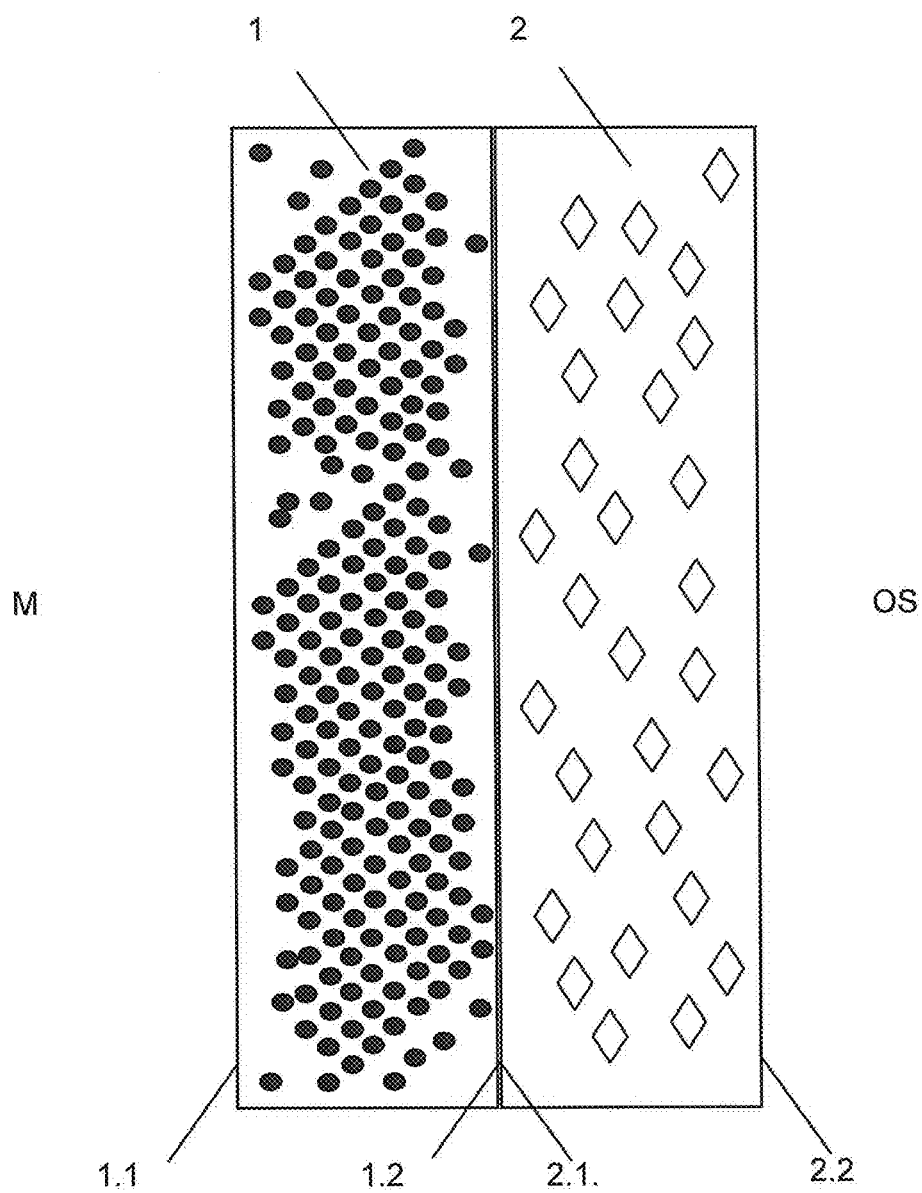
FIG. 1 shows a two-layer construction of the sensor element according to the invention.

FIG. 1 shows a two-layer construction of the sensor element according to the invention, comprising an indicator protector (•) bearing layer (1) and an indicator (◊) bearing layer (2). Layer (1) contacts the medium (M), and layer (2) is coupled with the optical system (OS).

Figure 2:
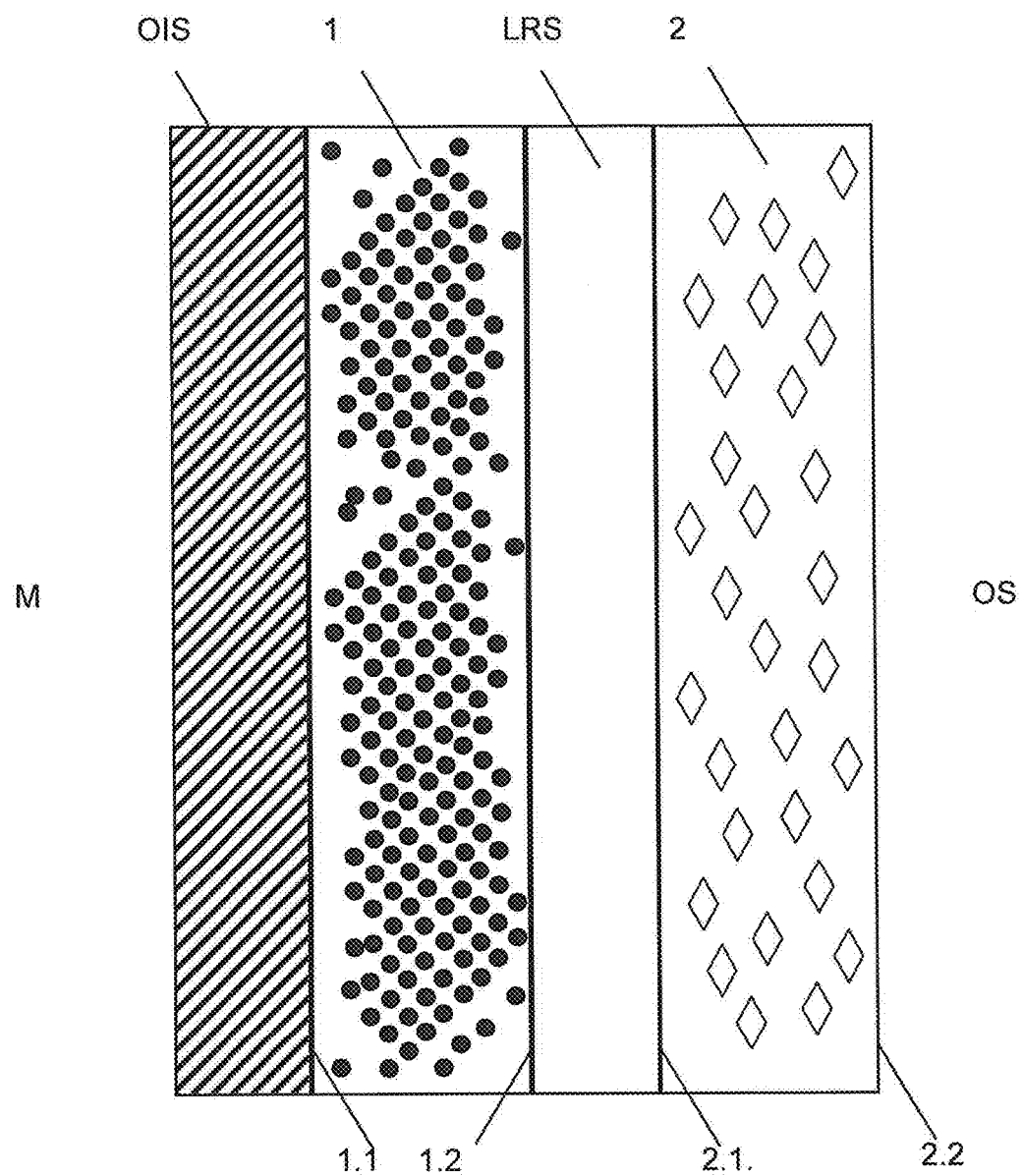
FIG. 2 shows a four-layer construction of the sensor element according to the invention.

FIG. 2 shows a four-layer construction of the sensor element according to the invention, comprising an indicator protector (•) bearing layer (1) and an indicator (◊) bearing layer (2). Layer (2) is coupled with the optical system (OS). There is a light-reflecting layer (LRS) situated between layers (1) and (2). An optical isolation layer (OIS), which contacts the medium (M), is applied to side (1.1) of layer (1).

EXAMPLE 1

In the outer layer of a three-layer silicone membrane for an oxygen sensor, 20 percent by weight, relative to the mass of the wetted layer, of activated carbon particles with a diameter of 10-50 microns were immobilized. The procedure for this was as follows:

The prepolymer for the first membrane layer was weighed and mixed with a certain amount of a solvent. Subsequently, the activated carbon particles were added to the mixture and the entire mass was mixed. Thereafter, the polymer mixture was placed on a smooth surface, generating an approximately 150 micron thick layer. After the solvent was evaporated, the layer was ready to have further layers built up on it. The other layers were constructed in accordance with methods known to specialists in the field. A small circle of the sensor membrane fabricated in this way was bonded to the glass surface of a VisiFerm sensor cap, so that the sensory layer of the constructed membrane is facing toward the excitation light source of the sensor. To test the effect of the invention, the stability of the sensing membrane described here against attack by dissolved chlorine was compared with that of a conventional membrane, such as the one presently marketed by the applicant for the optical sensor "VisiFerm".

As described above, the destruction of the luminescence indicator is clearly reflected in the change of the relationship between the measured phase angle and oxygen partial pressure. This is also particularly true for the phase angle that is measured in an oxygen-free sensor environment, because the luminescence quenching takes place only in the presence of oxygen. The phase angle determined there is therefore particularly suitable for detecting a relevant change in the sensory properties and for examining the stability of the sensor membrane. For comparison, two identically constructed sensors were used, with one sensor having a conventional membrane, and the other being fitted with the membrane according to the invention. Both sensors were connected to a data acquisition system for recording the measured phase angle and simultaneously installed in a reaction vessel filled with 0.1 M hydrochloric acid. To record the initial situation, the medium in the reaction vessel was first purged with nitrogen to remove dissolved oxygen from the medium. The corresponding phase angles were measured with both sensors. Thereafter, a uniform 0.1% sodium hypochlorite solution was continuously added to the hydrochloric acid by means of a dosing apparatus, while constantly stirring, so that both sensors were exposed to the same definite volume of dissolved chlorine generated by the procedure. After 15 minutes the supply of sodium hypochlorite was stopped and the solution was again purged with nitrogen to expel the generated chlorine as well as any newly registered oxygen from the solution. Then the phase angle was recorded again. The chlorine exposure and nitrogenization was repeated four times.

Figure 3:
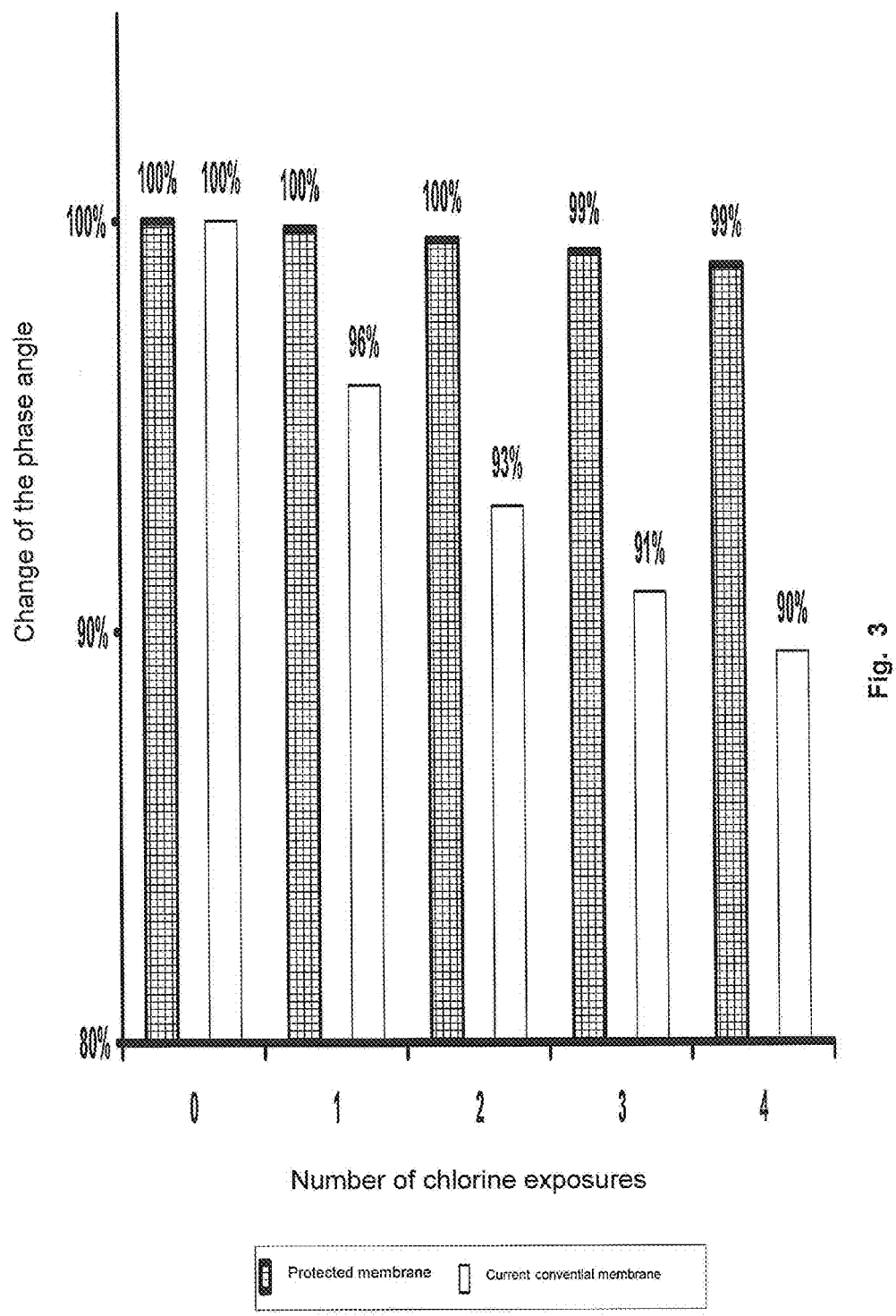
FIG. 3 shows the changes in the phase angle between a sensor element according to the invention and a sensor element known from the prior art, in each case following exposure to chlorine in a chlorine-free and oxygen-free environment.

FIG. 3 shows the changes in the phase angle of the two sensors, in each case measured after a chlorine exposure in a chlorine-free and oxygen-free environment, in reference to the initial situation. In the case of the conventional sensor membrane, the phase angle measured in an oxygen-free sensor environment decreased after four exposures to 90% of its initial value, while in the case of the protected membrane, the phase angle remained almost unchanged. If this phase angle falls by about 10% or more, the sensor membrane becomes unusable, because the Stern-Volmer relation is no longer accurate enough and/or cannot be determined accurately enough. This is the case after the fourth chlorine exposure of the conventional membrane. As the comparison clearly demonstrates, the sensor membrane according to the invention is significantly more stable against an oxidative attack by chlorine and is still fully functional after four attacks.

EXAMPLE 2

Analogously to example 1, a sensor membrane was evaluated in regard to its ozone resistance. The sensor membrane was constructed with 25 percent by weight activated carbon, relative to the layer in contact with the medium. To test the effect of the invention, the stability of the sensor membrane against an attack by dissolved ozone was compared to that of a conventional membrane in a manner similar to that described above. For this purpose, pure oxygen was passed through one of the ozonizers and the gas mixture was directed into a reaction vessel filled with water, in which a sensor with a conventional membrane and a sensor with a membrane according to the invention were fitted, for about two hours. As can be seen from FIG. 4, in the case of the conventional sensor membrane the phase angle decreased to about 95% of its initial value following ozone exposure in an oxygen-free environment, whereas the phase angle remained unchanged in the case of the membrane protected in accordance with the invention. As this comparison shows, the sensor membrane according to the invention is also significantly more stable against an oxidative attack by ozone.

The invention is particularly suitable for the measurement of dissolved oxygen when strong oxidative substances, such as those used, e.g., for disinfection, which totally or partially destroy conventional membranes in a short time, are present in the medium.

What is claimed is:

1. An optical sensor element comprising:
at least one indicator composed of a luminescence-active agent; and
at least one indicator protector,
characterized in that the element comprises at least one indicator-bearing layer and at least one indicator protector-bearing layer, with the at least one indicator protector arranged in a layer of the element that faces towards a medium and the at least one indicator arranged in at least one different layer that is mounted facing away from the medium,
wherein the element comprises i) an opaque first layer in contact with the medium, which is substantially free of indicators, ii) a second layer comprising the at least one indicator protector-bearing layer, which iia) is mounted on the side of the first layer that faces away from the medium, iib) contains indicator protectors, and iic) is substantially free of indicators, iii) a third layer comprising the at least one indicator-bearing layer, which iiia) is mounted on the side of the second layer that faces away from the medium, iiib) contains the indicators, and iiic) is substantially free of indicator protectors,
wherein the indicator protectors are selected from a) reducing agents and/or catalysts for the reduction of strong oxidants, b) adsorbents for chemisorption or physisorption of strong oxidants, or c) a combination of a) and b).

2. An optical sensor element comprising:
at least one indicator composed of a luminescence-active agent; and
at least one indicator protector,
characterized in that the element comprises at least one indicator-bearing layer and at least one indicator protector-bearing layer, with the at least one indicator protector arranged in a layer of the element that faces towards the medium and the at least one indicator arranged in at least one layer which is mounted facing away from the medium,
wherein the indicator protectors are selected from a) reducing agents and/or catalysts for the reduction of strong oxidants, b) adsorbents for chemisorption or physisorption of strong oxidants, or c) a combination of a) and b) and the indicator protector-bearing layer(s) are separated from the indicator-bearing layer(s) by at least one light-reflecting layer.

3. A sensor comprising:
an optical sensor element as claimed in claim 1;
an energy source that excites the luminescent emission of the indicators; and
a detection unit operatively connected to receive the luminescent emission of the indicators.

* * * * *